(12) United States Patent
Hoarau

(10) Patent No.: US 7,899,510 B2
(45) Date of Patent: Mar. 1, 2011

(54) MEDICAL SENSOR AND TECHNIQUE FOR USING THE SAME

(75) Inventor: Carine Hoarau, Lafayette, CA (US)

(73) Assignee: Nellcor Puritan Bennett LLC, Boulder, CO (US)

(*) Notice: Subject to any disclaimer, the term of this patent is extended or adjusted under 35 U.S.C. 154(b) by 1463 days.

(21) Appl. No.: 11/241,424

(22) Filed: Sep. 29, 2005

(65) Prior Publication Data

US 2007/0073122 A1    Mar. 29, 2007

(51) Int. Cl.
*A61B 5/1455*    (2006.01)
(52) U.S. Cl. .................. 600/344; 600/310; 600/323
(58) Field of Classification Search ........... 600/310, 600/323, 344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger |
| 4,694,833 A | 9/1987 | Hamaguri |

(Continued)

FOREIGN PATENT DOCUMENTS

DE    3405444    8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
(74) *Attorney, Agent, or Firm*—Fletcher Yoder

(57) ABSTRACT

A sensor may be adapted to account for factors that cause irregularities in sensor measurements. A sensor may selectively absorb light from outside sources. A sensor may selectively absorb light near a region of tissue having relatively large subcutaneous anatomic structures, such as large blood vessels, and selectively reflect light near a region of tissue that is relatively free of large blood vessels or other structures. The sensor is adapted to reduce the effect of large subcutaneous anatomic structures and outside light on measurements for pulse oximetry or other spectrophotometric techniques.

60 Claims, 8 Drawing Sheets

U.S. PATENT DOCUMENTS

| | | | |
|---|---|---|---|
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE033,643 E | 7/1991 | Isaacson et al. |
| 5,028,787 A | 7/1991 | Rosenthal et al. |
| 5,035,243 A | 7/1991 | Muz |
| 5,040,536 A | 8/1991 | Riff |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |

| Patent No. | Date | Inventor |
|---|---|---|
| 5,348,005 A | 9/1994 | Merrick et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE035,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,790,729 A | 8/1998 | Pologe et al. |

| | | | | | |
|---|---|---|---|---|---|
| 5,792,052 A | 8/1998 | Isaacson et al. | 5,978,693 A | 11/1999 | Hamilton et al. |
| 5,795,292 A | 8/1998 | Lewis et al. | 5,983,120 A | 11/1999 | Groner et al. |
| 5,797,841 A | 8/1998 | DeLonzor et al. | 5,983,122 A | 11/1999 | Jarman et al. |
| 5,800,348 A | 9/1998 | Kaestle | 5,987,343 A | 11/1999 | Kinast |
| 5,800,349 A | 9/1998 | Isaacson et al. | 5,991,648 A | 11/1999 | Levin |
| 5,803,910 A | 9/1998 | Potratz | 5,995,855 A | 11/1999 | Kiani et al. |
| 5,807,246 A | 9/1998 | Sakaguchi et al. | 5,995,856 A | 11/1999 | Mannheimer et al. |
| 5,807,247 A | 9/1998 | Merchant et al. | 5,995,858 A | 11/1999 | Kinast |
| 5,807,248 A | 9/1998 | Mills | 5,995,859 A | 11/1999 | Takahashi |
| 5,810,723 A | 9/1998 | Aldrich | 5,997,343 A | 12/1999 | Mills et al. |
| 5,810,724 A | 9/1998 | Gronvall | 5,999,834 A | 12/1999 | Wang et al. |
| 5,813,403 A * | 9/1998 | Soller et al. .................. 600/310 | 6,002,952 A | 12/1999 | Diab et al. |
| 5,813,980 A | 9/1998 | Levinson et al. | 6,005,658 A | 12/1999 | Kaluza et al. |
| 5,817,008 A | 10/1998 | Rafert et al. | 6,006,120 A | 12/1999 | Levin |
| 5,817,009 A | 10/1998 | Rosenheimer et al. | 6,011,985 A | 1/2000 | Athan et al. |
| 5,817,010 A | 10/1998 | Hibl | 6,011,986 A | 1/2000 | Diab et al. |
| 5,818,985 A | 10/1998 | Merchant et al. | 6,014,576 A | 1/2000 | Raley et al. |
| 5,820,550 A | 10/1998 | Polson et al. | 6,018,673 A | 1/2000 | Chin et al. |
| 5,823,950 A | 10/1998 | Diab et al. | 6,018,674 A | 1/2000 | Aronow |
| 5,823,952 A | 10/1998 | Levinson et al. | 6,022,321 A | 2/2000 | Amano et al. |
| 5,825,488 A * | 10/1998 | Kohl et al. .................. 600/310 | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE036,000 E | 12/1998 | Swedlow et al. | 6,047,201 A | 4/2000 | Jackson, III |
| 5,842,979 A | 12/1998 | Jarman et al. | 6,055,447 A | 4/2000 | Well |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjany et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura et al. |
| 5,924,982 A | 7/1999 | Chin | 6,157,850 A | 12/2000 | Diab et al. |
| 5,924,985 A | 7/1999 | Jones | 6,159,147 A | 12/2000 | Lichter |
| 5,934,277 A | 8/1999 | Mortz | 6,163,715 A | 12/2000 | Larsen et al. |
| 5,934,925 A | 8/1999 | Tobler et al. | 6,165,005 A | 12/2000 | Mills et al. |
| 5,940,182 A | 8/1999 | Lepper, Jr. et al. | 6,173,196 B1 | 1/2001 | Delonzor et al. |
| 5,954,644 A | 9/1999 | Dettling et al. | 6,178,343 B1 | 1/2001 | Bindszus et al. |
| 5,957,840 A | 9/1999 | Terasawa et al. | 6,179,159 B1 | 1/2001 | Gurley |
| 5,960,610 A | 10/1999 | Levinson et al. | 6,181,958 B1 | 1/2001 | Steuer et al. |
| 5,961,450 A | 10/1999 | Merchant et al. | 6,181,959 B1 | 1/2001 | Schöllerman et al. |
| 5,961,452 A | 10/1999 | Chung et al. | 6,184,521 B1 | 2/2001 | Coffin, IV et al. |
| 5,964,701 A | 10/1999 | Asada et al. | 6,188,470 B1 | 2/2001 | Grace |
| 5,971,930 A | 10/1999 | Elghazzawi | 6,192,260 B1 | 2/2001 | Chance |
| 5,978,691 A | 11/1999 | Mills | 6,195,575 B1 | 2/2001 | Levinson |

| | | | | | | |
|---|---|---|---|---|---|---|
| 6,198,951 | B1 | 3/2001 | Kosuda et al. | 6,430,513 | B1 | 8/2002 | Wang et al. |
| 6,206,830 | B1 | 3/2001 | Diab et al. | 6,430,525 | B1 | 8/2002 | Weber et al. |
| 6,213,952 | B1 | 4/2001 | Finarov et al. | 6,434,408 | B1 | 8/2002 | Heckel et al. |
| 6,217,523 | B1 | 4/2001 | Amano et al. | 6,438,396 | B1 | 8/2002 | Cook |
| 6,222,189 | B1 | 4/2001 | Misner et al. | 6,438,399 | B1 | 8/2002 | Kurth |
| 6,223,064 | B1 | 4/2001 | Lynn | 6,449,501 | B1 | 9/2002 | Reuss |
| 6,226,539 | B1 | 5/2001 | Potratz | 6,453,183 | B1 | 9/2002 | Walker |
| 6,226,540 | B1 | 5/2001 | Bernreuter et al. | 6,453,184 | B1 | 9/2002 | Hyogo et al. |
| 6,229,856 | B1 | 5/2001 | Diab et al. | 6,456,862 | B2 | 9/2002 | Benni |
| 6,230,035 | B1 | 5/2001 | Aoyagi et al. | 6,461,305 | B1 | 10/2002 | Schnall |
| 6,233,470 | B1 | 5/2001 | Tsuchiya | 6,463,310 | B1 | 10/2002 | Swedlow et al. |
| 6,236,871 | B1 | 5/2001 | Tsuchiya | 6,463,311 | B1 | 10/2002 | Diab |
| 6,236,872 | B1 | 5/2001 | Diab et al. | 6,466,808 | B1 | 10/2002 | Chin et al. |
| 6,240,305 | B1 | 5/2001 | Tsuchiya | 6,466,809 | B1 | 10/2002 | Riley |
| 6,253,097 | B1 | 6/2001 | Aronow et al. | 6,470,199 | B1 | 10/2002 | Kopotic et al. |
| 6,253,098 | B1 | 6/2001 | Walker et al. | 6,470,200 | B1 | 10/2002 | Walker et al. |
| 6,256,523 | B1 | 7/2001 | Diab et al. | 6,480,729 | B2 | 11/2002 | Stone |
| 6,256,524 | B1 | 7/2001 | Walker et al. | 6,490,466 | B1 | 12/2002 | Fein et al. |
| 6,261,236 | B1 | 7/2001 | Grimblatov | 6,493,568 | B1 | 12/2002 | Bell |
| 6,263,221 | B1 | 7/2001 | Chance et al. | 6,496,711 | B1 | 12/2002 | Athan et al. |
| 6,263,222 | B1 | 7/2001 | Diab et al. | 6,498,942 | B1 | 12/2002 | Esenaliev et al. |
| 6,263,223 | B1 | 7/2001 | Sheperd et al. | 6,501,974 | B2 | 12/2002 | Huiku |
| 6,266,546 | B1 | 7/2001 | Steuer et al. | 6,501,975 | B2 | 12/2002 | Diab et al. |
| 6,266,547 | B1 | 7/2001 | Walker et al. | 6,505,060 | B1 | 1/2003 | Norris |
| 6,272,363 | B1 | 8/2001 | Casciani et al. | 6,505,061 | B2 | 1/2003 | Larson |
| 6,278,522 | B1 | 8/2001 | Lepper, Jr. et al. | 6,505,133 | B1 | 1/2003 | Hanna et al. |
| 6,280,213 | B1 | 8/2001 | Tobler et al. | 6,510,329 | B2 | 1/2003 | Heckel |
| 6,280,381 | B1 | 8/2001 | Malin et al. | 6,510,331 | B1 | 1/2003 | Williams et al. |
| 6,285,894 | B1 | 9/2001 | Oppelt et al. | 6,512,937 | B2 | 1/2003 | Blank et al. |
| 6,285,895 | B1 | 9/2001 | Ristolainen et al. | 6,515,273 | B2 | 2/2003 | Al-Ali |
| 6,285,896 | B1 | 9/2001 | Tobler et al. | 6,519,484 | B1 | 2/2003 | Lovejoy et al. |
| 6,298,252 | B1 | 10/2001 | Kovach et al. | 6,519,486 | B1 | 2/2003 | Edgar, Jr. et al. |
| 6,308,089 | B1 | 10/2001 | Von der Ruhr et al. | 6,519,487 | B1 | 2/2003 | Parker |
| 6,321,100 | B1 | 11/2001 | Parker | 6,525,386 | B1 | 2/2003 | Mills et al. |
| 6,330,468 | B1 | 12/2001 | Scharf | 6,526,300 | B1 | 2/2003 | Kiani et al. |
| 6,334,065 | B1 | 12/2001 | Al-Ali et al. | 6,526,301 | B2 | 2/2003 | Larsen et al. |
| 6,339,715 | B1 | 1/2002 | Bahr et al. | 6,541,756 | B2 | 4/2003 | Schulz et al. |
| 6,342,039 | B1 | 1/2002 | Lynn | 6,542,764 | B1 | 4/2003 | Al-Ali et al. |
| 6,343,223 | B1 | 1/2002 | Chin et al. | 6,546,267 | B1 | 4/2003 | Sugiura et al. |
| 6,343,224 | B1 | 1/2002 | Parker | 6,553,241 | B2 | 4/2003 | Mannheimer et al. |
| 6,349,228 | B1 | 2/2002 | Kiani et al. | 6,553,242 | B1 | 4/2003 | Sarussi |
| 6,351,658 | B1 | 2/2002 | Middleman et al. | 6,553,243 | B2 | 4/2003 | Gurley |
| 6,353,750 | B1 | 3/2002 | Kimura | 6,554,788 | B1 | 4/2003 | Hunley |
| 6,356,774 | B1 | 3/2002 | Bernstein et al. | 6,556,852 | B1 | 4/2003 | Schulze et al. |
| 6,360,113 | B1 | 3/2002 | Dettling | 6,560,470 | B1 | 5/2003 | Pologe |
| 6,360,114 | B1 | 3/2002 | Diab et al. | 6,564,077 | B2 | 5/2003 | Mortara |
| 6,361,501 | B1 | 3/2002 | Amano et al. | 6,564,088 | B1 | 5/2003 | Soller et al. |
| 6,363,269 | B1 | 3/2002 | Hanna et al. | 6,571,113 | B1 | 5/2003 | Fein et al. |
| D455,834 | S | 4/2002 | Donars et al. | 6,571,114 | B1 | 5/2003 | Koike et al. |
| 6,370,408 | B1 | 4/2002 | Merchant et al. | 6,574,491 | B2 | 6/2003 | Elghazzawi |
| 6,370,409 | B1 | 4/2002 | Chung et al. | 6,580,086 | B1 | 6/2003 | Schulz et al. |
| 6,371,921 | B1 | 4/2002 | Caro | 6,584,336 | B1 | 6/2003 | Ali et al. |
| 6,374,129 | B1 | 4/2002 | Chin et al. | 6,587,703 | B2 | 7/2003 | Cheng et al. |
| 6,377,829 | B1 | 4/2002 | Al-Ali et al. | 6,587,704 | B1 | 7/2003 | Fine et al. |
| 6,381,479 | B1 | 4/2002 | Norris | 6,589,172 | B2 | 7/2003 | Williams et al. |
| 6,381,480 | B1 | 4/2002 | Stoddar et al. | 6,591,122 | B2 | 7/2003 | Schmitt |
| 6,385,471 | B1 | 5/2002 | Mortz | 6,591,123 | B2 | 7/2003 | Fein et al. |
| 6,385,821 | B1 | 5/2002 | Modgil et al. | 6,594,511 | B2 | 7/2003 | Stone et al. |
| 6,388,240 | B2 | 5/2002 | Schulz et al. | 6,594,512 | B2 | 7/2003 | Huang |
| 6,393,310 | B1 | 5/2002 | Kuenstner | 6,594,513 | B1 | 7/2003 | Jobsis et al. |
| 6,393,311 | B1 | 5/2002 | Edgar, Jr. et al. | 6,597,931 | B1 | 7/2003 | Cheng et al. |
| 6,397,091 | B2 | 5/2002 | Diab et al. | 6,597,933 | B2 | 7/2003 | Kiani et al. |
| 6,397,092 | B1 | 5/2002 | Norris et al. | 6,600,940 | B1 | 7/2003 | Fein et al. |
| 6,397,093 | B1 | 5/2002 | Aldrich | 6,606,510 | B2 | 8/2003 | Swedlow et al. |
| 6,400,971 | B1 | 6/2002 | Finarov et al. | 6,606,511 | B1 | 8/2003 | Ali et al. |
| 6,400,972 | B1 | 6/2002 | Fine | 6,606,512 | B2 | 8/2003 | Muz et al. |
| 6,400,973 | B1 | 6/2002 | Winter | 6,608,562 | B1 | 8/2003 | Kimura et al. |
| 6,402,690 | B1 | 6/2002 | Rhee et al. | 6,609,016 | B1 | 8/2003 | Lynn |
| 6,408,198 | B1 | 6/2002 | Hanna et al. | 6,615,064 | B1 | 9/2003 | Aldrich |
| 6,411,832 | B1 | 6/2002 | Guthermann | 6,615,065 | B1 | 9/2003 | Barrett et al. |
| 6,411,833 | B1 | 6/2002 | Baker, Jr. et al. | 6,618,602 | B2 | 9/2003 | Levin et al. |
| 6,421,549 | B1 | 7/2002 | Jacques | 6,622,034 | B1 | 9/2003 | Gorski et al. |
| 6,430,423 | B2 | 8/2002 | DeLonzor et al. | 6,628,975 | B1 | 9/2003 | Fein et al. |

| | | | |
|---|---|---|---|
| 6,631,281 B1 | 10/2003 | Kästle | |
| 6,632,181 B2 | 10/2003 | Flaherty | |
| 6,640,116 B2 | 10/2003 | Diab | |
| 6,643,530 B2 | 11/2003 | Diab et al. | |
| 6,643,531 B1 | 11/2003 | Katarow | |
| 6,647,279 B2 | 11/2003 | Pologe | |
| 6,647,280 B2 | 11/2003 | Bahr et al. | |
| 6,650,916 B2 | 11/2003 | Cook | |
| 6,650,917 B2 | 11/2003 | Diab et al. | |
| 6,650,918 B2 | 11/2003 | Terry | |
| 6,654,621 B2 | 11/2003 | Palatnik et al. | |
| 6,654,622 B1 | 11/2003 | Eberhard et al. | |
| 6,654,623 B1 | 11/2003 | Kästle | |
| 6,654,624 B2 | 11/2003 | Diab et al. | |
| 6,658,276 B2 | 12/2003 | Kianl et al. | |
| 6,658,277 B2 | 12/2003 | Wassermann | |
| 6,662,033 B2 | 12/2003 | Casciani et al. | |
| 6,665,551 B1 | 12/2003 | Suzuki | |
| 6,668,182 B2 | 12/2003 | Hubelbank | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,671,530 B2 | 12/2003 | Chung et al. | |
| 6,671,531 B2 | 12/2003 | Al-Ali et al. | |
| 6,671,532 B1 | 12/2003 | Fudge et al. | |
| 6,675,031 B1 | 1/2004 | Porges et al. | |
| 6,678,543 B2 | 1/2004 | Diab et al. | |
| 6,681,126 B2 | 1/2004 | Solenberger | |
| 6,681,128 B2 | 1/2004 | Steuer et al. | |
| 6,681,454 B2 | 1/2004 | Modgil et al. | |
| 6,684,090 B2 | 1/2004 | Ali et al. | |
| 6,684,091 B2 | 1/2004 | Parker | |
| 6,694,160 B2 | 2/2004 | Chin | |
| 6,697,653 B2 | 2/2004 | Hanna | |
| 6,697,655 B2 | 2/2004 | Sueppel et al. | |
| 6,697,656 B1 | 2/2004 | Al-Ali | |
| 6,697,658 B2 | 2/2004 | Al-Ali | |
| RE038,476 E | 3/2004 | Diab et al. | |
| 6,699,194 B1 | 3/2004 | Diab et al. | |
| 6,699,199 B2 | 3/2004 | Asada et al. | |
| 6,701,170 B2 | 3/2004 | Stetson | |
| 6,702,752 B2 | 3/2004 | Dekker | |
| 6,707,257 B2 | 3/2004 | Norris | |
| 6,708,049 B1 | 3/2004 | Berson et al. | |
| 6,709,402 B2 | 3/2004 | Dekker | |
| 6,711,424 B1 | 3/2004 | Fine et al. | |
| 6,711,425 B1 | 3/2004 | Reuss | |
| 6,712,762 B1 | 3/2004 | Lichter | |
| 6,714,803 B1 | 3/2004 | Mortz | |
| 6,714,804 B2 | 3/2004 | Al-Ali et al. | |
| 6,714,805 B2 | 3/2004 | Jeon et al. | |
| RE038,492 E | 4/2004 | Diab et al. | |
| 6,719,686 B2 | 4/2004 | Coakley et al. | |
| 6,719,705 B2 | 4/2004 | Mills | |
| 6,720,734 B2 | 4/2004 | Norris | |
| 6,721,584 B2 | 4/2004 | Baker, Jr. et al. | |
| 6,721,585 B1 | 4/2004 | Parker | |
| 6,725,074 B1 | 4/2004 | Kästle | |
| 6,725,075 B2 | 4/2004 | Al-Ali | |
| 6,731,962 B1 | 5/2004 | Katarow | |
| 6,731,963 B2 | 5/2004 | Finarov et al. | |
| 6,731,967 B1 | 5/2004 | Turcott | |
| 6,735,459 B2 | 5/2004 | Parker | |
| 6,745,060 B2 | 6/2004 | Diab et al. | |
| 6,745,061 B1 | 6/2004 | Hicks et al. | |
| 6,748,253 B2 | 6/2004 | Norris et al. | |
| 6,748,254 B2 | 6/2004 | O'Neill et al. | |
| 6,754,515 B1 | 6/2004 | Pologe | |
| 6,754,516 B2 | 6/2004 | Mannheimer | |
| 6,760,607 B2 | 7/2004 | Al-Ali | |
| 6,760,609 B2 | 7/2004 | Jacques | |
| 6,760,610 B2 | 7/2004 | Tschupp et al. | |
| 6,763,255 B2 | 7/2004 | DeLonzor et al. | |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |

| Patent/Pub No. | Date | Name |
|---|---|---|
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Liu et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,280,858 B2 | 10/2007 | Al-Ali et al. |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173708 A1 * | 11/2002 | DeLonzor et al. ............ 600/323 |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0197548 A1 | 9/2005 | Dietiker |
| 2005/0228248 A1 | 10/2005 | Dietiker |
| 2005/0256386 A1 | 11/2005 | Chan |
| 2005/0272986 A1 | 12/2005 | Smith |
| 2005/0277819 A1 | 12/2005 | Kiani et al. |
| 2006/0020179 A1 | 1/2006 | Anderson |
| 2006/0030764 A1 | 2/2006 | Porge |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2006/0224058 A1 * | 10/2006 | Mannheimer ............ 600/323 |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0260129 A1 | 11/2007 | Chin |
| 2007/0260130 A1 | 11/2007 | Chin |
| 2007/0260131 A1 | 11/2007 | Chin |
| 2007/0299328 A1 | 12/2007 | Chin et al. |

FOREIGN PATENT DOCUMENTS

| | | |
|---|---|---|
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 00204459 | 12/1986 |
| EP | 0 262 779 | 4/1988 |
| EP | 0315040 | 10/1988 |
| EP | 0314331 | 5/1989 |

| | | | | | |
|---|---|---|---|---|---|
| EP | 00352923 | 1/1990 | JP | 10337282 | 12/1998 |
| EP | 0 360 977 | 4/1990 | JP | 11019074 | 1/1999 |
| EP | 00430340 | 6/1991 | JP | 11155841 | 6/1999 |
| EP | 0435 500 | 7/1991 | JP | 11 188019 | 7/1999 |
| EP | 0572684 | 5/1992 | JP | 11244268 | 9/1999 |
| EP | 00497021 | 8/1992 | JP | 20107157 | 4/2000 |
| EP | 0529412 | 8/1992 | JP | 20237170 | 9/2000 |
| EP | 0531631 | 9/1992 | JP | 21245871 | 9/2001 |
| EP | 0566354 | 4/1993 | JP | 22224088 | 8/2002 |
| EP | 0587009 | 8/1993 | JP | 22282242 | 10/2002 |
| EP | 00630203 | 9/1993 | JP | 23153881 | 5/2003 |
| EP | 0 572 684 | 12/1993 | JP | 23153882 | 5/2003 |
| EP | 00615723 | 9/1994 | JP | 23169791 | 6/2003 |
| EP | 00702931 | 3/1996 | JP | 23194714 | 7/2003 |
| EP | 00724860 | 8/1996 | JP | 23210438 | 7/2003 |
| EP | 00793942 | 9/1997 | JP | 23275192 | 9/2003 |
| EP | 0 864 293 | 9/1998 | JP | 23339678 | 12/2003 |
| EP | 01006863 | 10/1998 | JP | 24008572 | 1/2004 |
| EP | 01006864 | 10/1998 | JP | 24089546 | 3/2004 |
| EP | 0875199 | 11/1998 | JP | 24113353 | 4/2004 |
| EP | 00998214 | 12/1998 | JP | 24135854 | 5/2004 |
| EP | 0 898 933 | 3/1999 | JP | 24148069 | 5/2004 |
| EP | 0898933 | 3/1999 | JP | 24148070 | 5/2004 |
| EP | 01332713 | 8/2003 | JP | 24159810 | 6/2004 |
| EP | 01469773 | 8/2003 | JP | 24166775 | 6/2004 |
| EP | 1502529 | 7/2004 | JP | 24194908 | 7/2004 |
| EP | 01491135 | 12/2004 | JP | 24202190 | 7/2004 |
| FR | 2685865 | 1/1992 | JP | 24248819 | 9/2004 |
| GB | 2 259 545 | 3/1993 | JP | 24248820 | 9/2004 |
| JP | 63275325 | 11/1988 | JP | 24261364 | 9/2004 |
| JP | 2013450 | 1/1990 | JP | 24290412 | 10/2004 |
| JP | 2111343 | 4/1990 | JP | 24290544 | 10/2004 |
| JP | 02 191434 | 7/1990 | JP | 24290545 | 10/2004 |
| JP | 2237544 | 9/1990 | JP | 24329406 | 11/2004 |
| JP | 03 173536 | 7/1991 | JP | 24329607 | 11/2004 |
| JP | 3170866 | 7/1991 | JP | 24329928 | 11/2004 |
| JP | 3245042 | 10/1991 | JP | 24337605 | 12/2004 |
| JP | 4174648 | 6/1992 | JP | 24344367 | 12/2004 |
| JP | 4191642 | 7/1992 | JP | 24351107 | 12/2004 |
| JP | 4332536 | 11/1992 | JP | 25034472 | 2/2005 |
| JP | 3124073 | 3/1993 | WO | WO 98/09566 | 10/1989 |
| JP | 5049624 | 3/1993 | WO | WO 90/01293 | 2/1990 |
| JP | 5049625 | 3/1993 | WO | WO 90/04352 | 5/1990 |
| JP | 3115374 | 4/1993 | WO | WO 91/01678 | 2/1991 |
| JP | 05 200031 | 8/1993 | WO | WO 91/11137 | 8/1991 |
| JP | 2005/200031 | 8/1993 | WO | WO 92/00513 | 1/1992 |
| JP | 5212016 | 8/1993 | WO | WO 92/21281 | 12/1992 |
| JP | 06 014906 | 1/1994 | WO | WO 93/09711 | 5/1993 |
| JP | 06014906 | 1/1994 | WO | WO 93/13706 | 7/1993 |
| JP | 6016774 | 3/1994 | WO | WO 93/16629 | 9/1993 |
| JP | 3116255 | 4/1994 | WO | WO 94/03102 | 2/1994 |
| JP | 6029504 | 4/1994 | WO | WO 94/23643 | 10/1994 |
| JP | 6098881 | 4/1994 | WO | WO 95/02358 | 1/1995 |
| JP | 06 154177 | 6/1994 | WO | WO 95/12349 | 5/1995 |
| JP | 6269430 | 9/1994 | WO | WO 95/16970 | 6/1995 |
| JP | 6285048 | 10/1994 | WO | WO 96/13208 | 5/1996 |
| JP | 7001273 | 1/1995 | WO | WO 96/13208 A | 5/1996 |
| JP | 7124138 | 5/1995 | WO | WO 96/39927 | 12/1996 |
| JP | 7136150 | 5/1995 | WO | WO 97/36536 | 10/1997 |
| JP | 3116259 | 6/1995 | WO | WO 97/36538 | 10/1997 |
| JP | 3116260 | 6/1995 | WO | WO 97/49330 | 12/1997 |
| JP | 7155311 | 6/1995 | WO | WO 98/17174 | 4/1998 |
| JP | 7155313 | 6/1995 | WO | WO 98/18382 | 5/1998 |
| JP | 3238813 | 7/1995 | WO | WO 98/18382 A | 5/1998 |
| JP | 7171139 | 7/1995 | WO | WO 98/43071 | 10/1998 |
| JP | 3134144 | 9/1995 | WO | WO 98/51212 | 11/1998 |
| JP | 7236625 | 9/1995 | WO | WO 98/57577 | 12/1998 |
| JP | 7246191 | 9/1995 | WO | WO 99/00053 | 1/1999 |
| JP | 8256996 | 10/1996 | WO | WO 99/32030 | 7/1999 |
| JP | 9192120 | 7/1997 | WO | WO 99/47039 | 9/1999 |
| JP | 10216113 | 8/1998 | WO | WO 99/63884 | 12/1999 |
| JP | 10216114 | 8/1998 | WO | WO 00/21438 | 4/2000 |
| JP | 10216115 | 8/1998 | WO | WO 00/28888 | 5/2000 |

| | | |
|---|---|---|
| WO | WO 00/59374 | 10/2000 |
| WO | WO 01/13790 | 3/2001 |
| WO | WO 01/13790 A | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/074162 A | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |
| WO | WO 2006/104790 A | 10/2006 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th-Nov. 2nd, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am. J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the $22^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the $22^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the*

26th *Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

\* cited by examiner

FIG. 2B
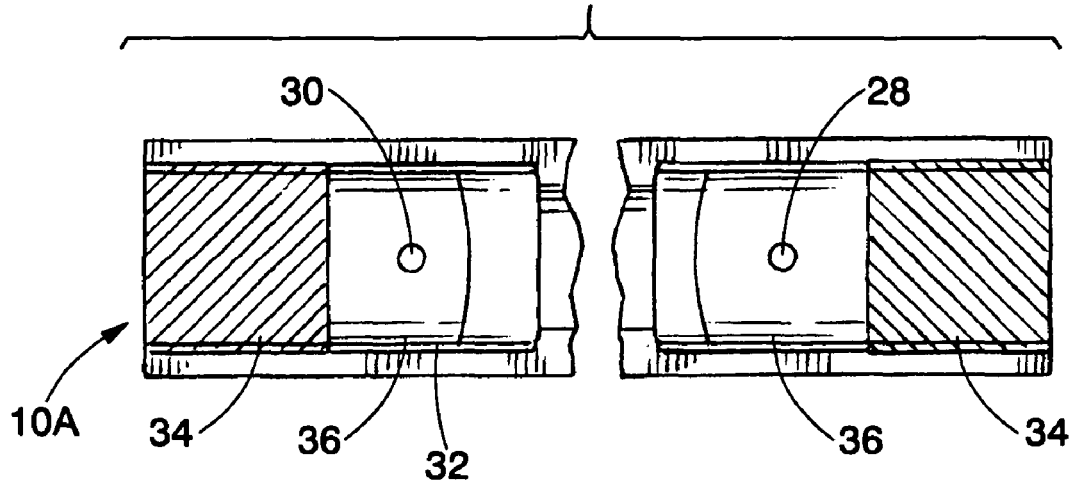
FIG. 2C
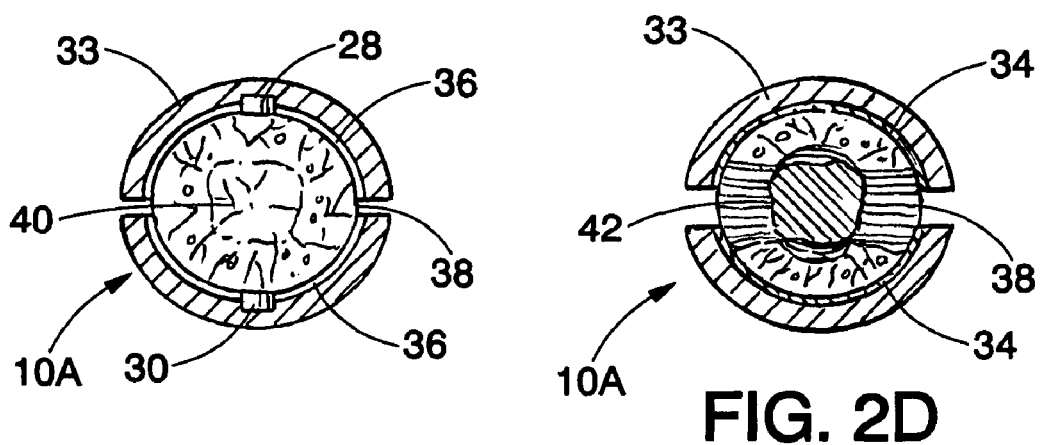
FIG. 2D
FIG. 2E
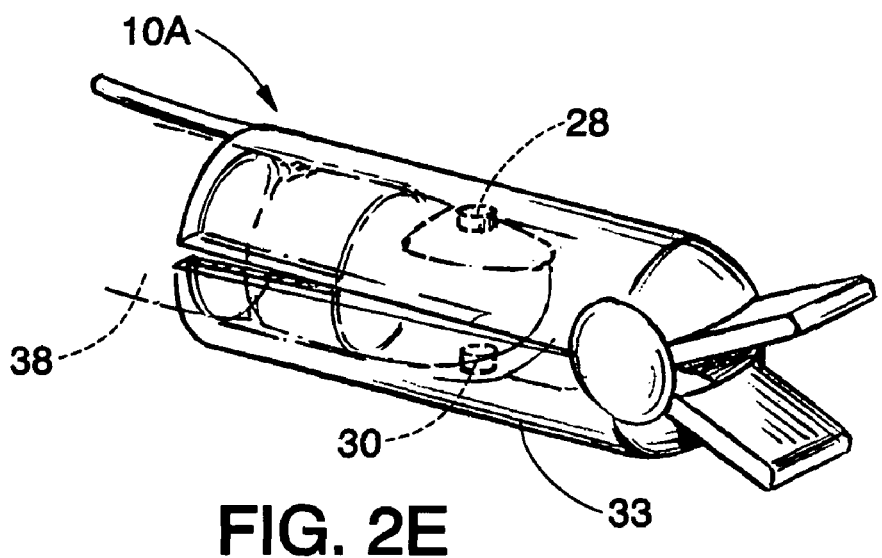

FIG. 4C
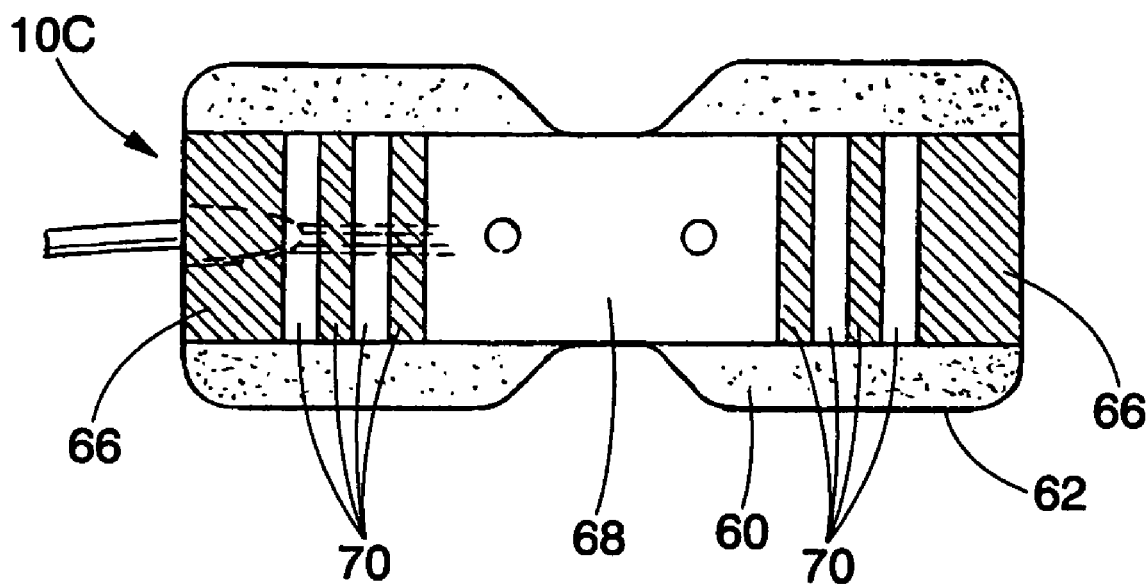
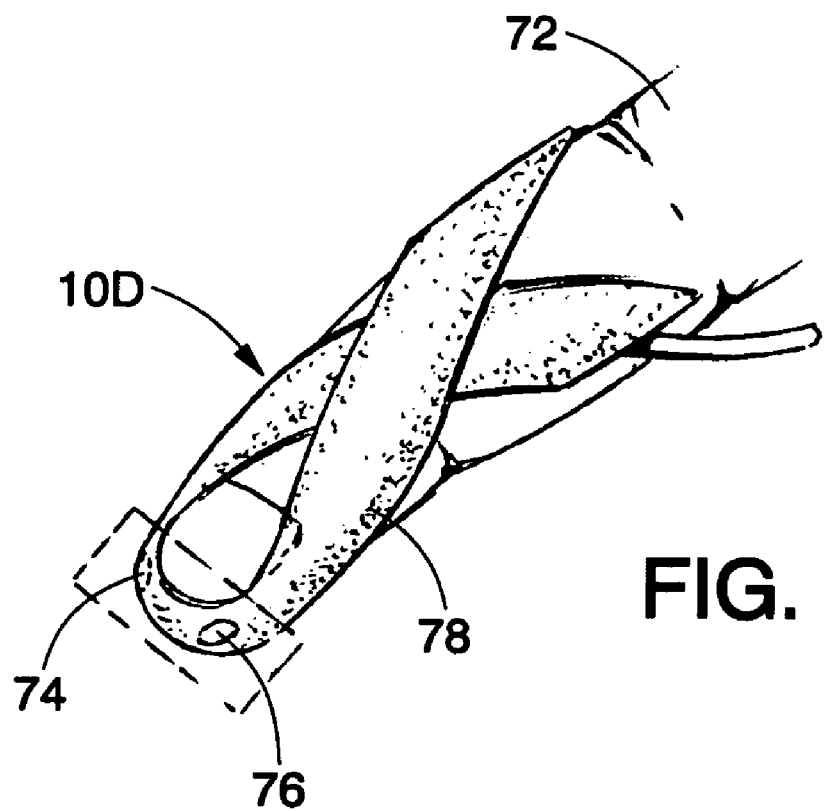
FIG. 5A

MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to certain aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry measures various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that emits light into a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount related to the amount of a blood constituent present in the blood. The amount of light absorbed and/or scattered may then be used to estimate the amount of the blood constituent in the tissue using various algorithms.

The pulse oximetry measurement depends in part on the assumptions that the contribution of outside light sources is negligible and that the detected light is transmitted through relatively homogeneous tissue. However, outside light may leak into a sensor, causing detection of light that is not related to the amount of blood constituent present in the blood. Additionally, these assumptions fail to take into account that human tissue is by nature heterogeneous, and that within any given tissue site there may be variations in the size and location of large blood vessels, bones, connective tissue, and other subcutaneous anatomic structures. These structures affect the path of the light as it passes through the tissue, causing measurement variations that do not relate to amount of the blood constituent.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; an emitter disposed on the sensor body, wherein the emitter is adapted to transmit light into tissue; a detector disposed on the sensor body, wherein the detector is adapted to detect the light; a light reflecting material disposed proximate to the emitter and detector on a first portion of a tissue-contacting surface of the sensor body; and a light absorbing material disposed on a second portion of the tissue-contacting surface of the sensor body.

There is provided a sensor that includes: an emitter adapted to deliver light into a tissue, wherein the tissue comprises relatively large subcutaneous anatomic structures and relatively small subcutaneous anatomic structures; a detector adapted to detect the light; and a sensor body on which the emitter and detector are disposed, the sensor body having a tissue-contacting surface, wherein the tissue-contacting surface is adapted to absorb light proximate to the relatively large subcutaneous anatomic structures and to reflect light proximate to the relatively small subcutaneous anatomic structures.

There is also provided a pulse oximetry system that includes a pulse oximetry monitor and a pulse oximetry sensor adapted to be operatively coupled to the monitor. The sensor includes a sensor body; an emitter disposed on the sensor body, wherein the emitter is adapted to transmit light into tissue; a detector disposed on the sensor body, wherein the detector is adapted to detect the light; a light reflecting material disposed proximate to the emitter and detector on a first portion of a tissue-contacting surface of the sensor body; and a light absorbing material disposed on a second portion of the tissue-contacting surface of the sensor body.

There is also provided a method of operating a sensor that includes: delivering light through a patient's tissue; absorbing the light with an absorptive material proximate to relatively large vascular structures; and reflecting the light with a reflective material proximate to relatively small vascular structures.

There is also provided a method of manufacturing a sensor that includes: providing a sensor body; providing an emitter adapted to transmit light into tissue; providing a detector adapted to detect the light; providing a light reflecting material disposed proximate to the emitter and detector on a first portion of a tissue-contacting surface of the sensor body; and providing a light absorbing material disposed on a second portion of the tissue-contacting surface of the sensor body.

There is also provided a method that includes: delivering light through a patient's tissue; and reflecting the light with a temperature-sensitive material adapted to have increased reflectivity when exposed to relatively low temperatures.

There is also provided a method that includes: delivering light through a patient's tissue; and absorbing the light with a material adapted to have increased absorption after receiving a feedback related to pressure.

BRIEF DESCRIPTION OF THE DRAWINGS

Advantages of the invention may become apparent upon reading the following detailed description and upon reference to the drawings in which:

FIG. 2B illustrates a top perspective view of the sensor of FIG. 2A in the open position;

FIG. 2C illustrates a fingertip cross-section of the sensor of FIG. 2A after placement on a patient's digit;

FIG. 2D illustrates a non-fingertip cross-section of the sensor of FIG. 2A after placement on a patient's digit;

FIG. 2E illustrates a perspective view of the sensor of FIG. 2A after application to a patient digit;

FIGS. 4B and 4C illustrate exemplary embodiments of transitional zones depicted with the sensor of FIG. 4A in accordance with the present invention;

FIG. 5A illustrates an exemplary embodiment of a wrap-style sensor in accordance with the present invention;

DETAILED DESCRIPTION OF SPECIFIC EMBODIMENTS

Figure 1:
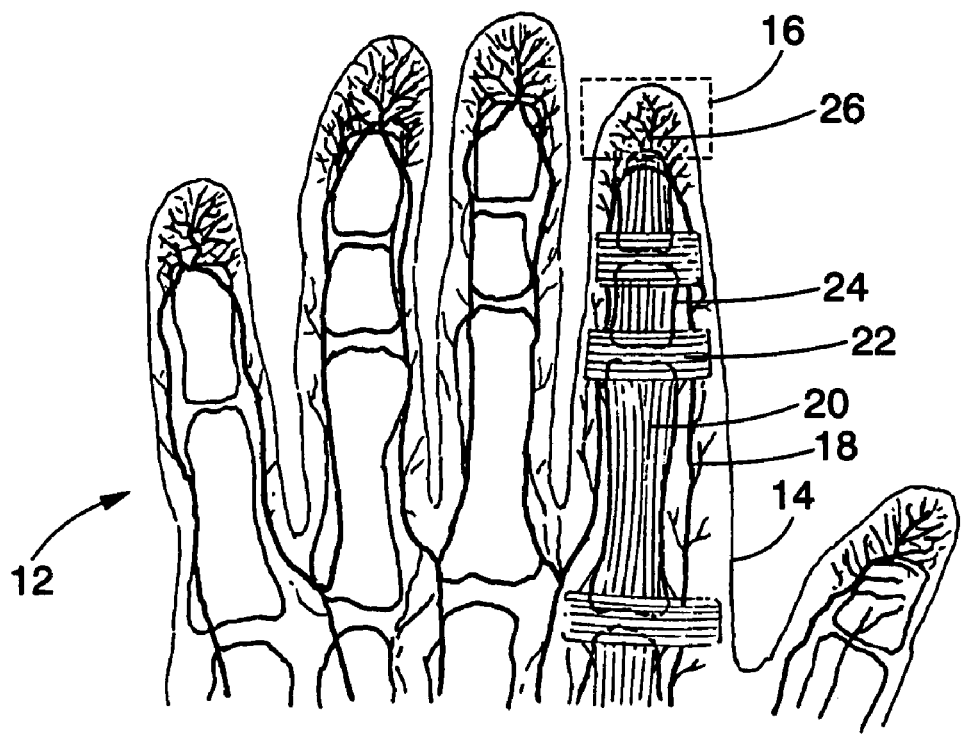
FIG. 1 illustrates an exemplary patient's finger illustrating the location of blood vessels, bone, and connective tissue.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to eliminate, reduce, or account for the possible influence of outside light sources and anatomic structures, which may cause variability in pulse oximetry measurements. For example, in accordance with some aspects of the present technique, sensors for pulse oximetry or other applications utilizing spectrophotometry are provided that reflect light proximate to areas of the tissue that do not contain dynamic anatomic structures, such as large blood vessels or connective tissue, thereby increasing the likelihood that the reflected light will be detected and provide useful data. In accordance with other aspects of the present technique, a sensor is provided that absorbs light proximate to dynamic anatomic structures, thereby preventing light modulated by the dynamic structures from being detected and providing erroneous or inaccurate data. Similarly, in accordance with other aspects of the present technique, a sensor absorbs outside light, i.e. light not provided by the sensor components that may leak into a sensor's interior.

Pulse oximetry sensors are typically placed on a patient in a location that is normally perfused with arterial blood to facilitate measurement of the desired blood characteristics, such as arterial oxygen saturation measurement ($SaO_2$). The most common sensor sites include a patient's fingertips, toes, earlobes, or forehead. Regardless of the placement of the sensor 10 used for pulse oximetry, the reliability of the pulse oximetry measurement is related to the accurate detection of transmitted light that has passed through the perfused tissue and has not been supplemented by outside light sources or unduly modulated by subcutaneous anatomic structures. Such supplementation and/or modulation of the light transmitted by the sensor 10 can cause variability in the resulting pulse oximetry measurements.

More specifically, light from the outside environment that is detected by the sensor 10 may adversely effect the measurement of the particular blood constituent, such as $SpO_2$. Additionally, larger blood vessels within the optically probed tissues may influence the relationship between the modulation ratio of the time-varying light transmission signals of the wavelengths transmitted and $SpO_2$. Thus, a sensor 10 may detect differences in signal modulations unrelated to the underlying $SaO_2$ level. In turn, this may impact the detected red-to-infrared modulation ratio and, consequently, the measured blood oxygen saturation ($SpO_2$) value. Other subcutaneous structures that may affect resulting pulse oximetry measurements include dynamic structures, which may move within the tissue. For example, connective tissue, such as tendons and ligaments, may move relative to bones during bending or flexing at joints. Larger blood vessels are also dynamic in response to arterial pressure. Changes in arterial pressure cause these vessels to expand, contract, and become distorted within the tissue. These dynamic structures may cause motion artifacts in pulse oximetry measurements. For example, when a patient bends a finger it may cause variations in the path of the light scattered and/or absorbed by the tendon during the bending movement. Additionally, surface structures of the finger may also affect the path of light. For example, the nail bed may change color when the finger presses down as blood pools under the nail. The skin may crease during finger motion, which may also affect the path of transmitted light.

By way of example, the hand structure 12 shown in FIG. 1 indicates that the density of larger diameter arteries in the digit 14 diminishes towards a fingertip region 16, which contain areas of relatively small vascular structures, including arterioles and capillaries. Thus, light transmitted through the distal end of the fingertips is not affected by the relatively large blood vessels present in other areas of the finger. In contrast, the relatively larger diameter arteries and tendons present in other areas contribute non-linearly to the optical density of the tissue. Hence, a sensor 10 designed to selectively absorb light near these larger diameter arteries, but to reflect light near the microvascular region of the fingertips would result in a reduction in variability of the $SaO_2$ measurement. Further, a sensor 10 designed to selectively absorb light near dynamic structures such as finger tendons, would result in a reduction in motion artifacts, which may also cause variability of the $SaO_2$ measurement.

Turning more specifically to FIG. 1, a digit 14 showing the locations of arteries 18, tendons 20, ligaments 22, and bone structure 24 is illustrated. These structures are much larger in diameter than the vasculature in the fingertip region 16 of the digit. Because the fingertip region contains relatively smaller vascular structures, the light from a pulse oximeter sensor will scatter through the tissue to probe the microvasculature 26, such as arterioles and capillaries, more uniformly, since the light fully penetrates these vessels. It is believed that this manner in which the light probes the more uniform tissue results in a more linear relationship between the modulating, i.e., cardiac-induced time-varying, optical density of the tissue and the underlying arterial blood oxygen saturation. As a result, the collected light presumably correlates better with the characteristics of the blood that the pulse oximeter is attempting to measure, since the collected light is not as adversely affected by strongly light-absorbing or scattering structures, such as bones, tendons, ligaments, and larger blood vessels.

Keeping in mind the preceding points, the following exemplary sensor designs are provided as examples of sensors that increase the amount of light collected by a sensor 10 while reducing or eliminating outside light and/or light modulated by dynamic anatomic structures. It should be appreciated that a sensor 10 according to the present teachings may be adapted for use on any digit, and may also be adapted for use on a forehead, earlobe, or other sensor site. For example, a sensor 10 may be a clip-style sensor, appropriate for a patient earlobe or digit. Alternatively, a sensor 10 may be a bandage-style or wrap-style sensor for use on a digit or forehead.

Figure 2A:
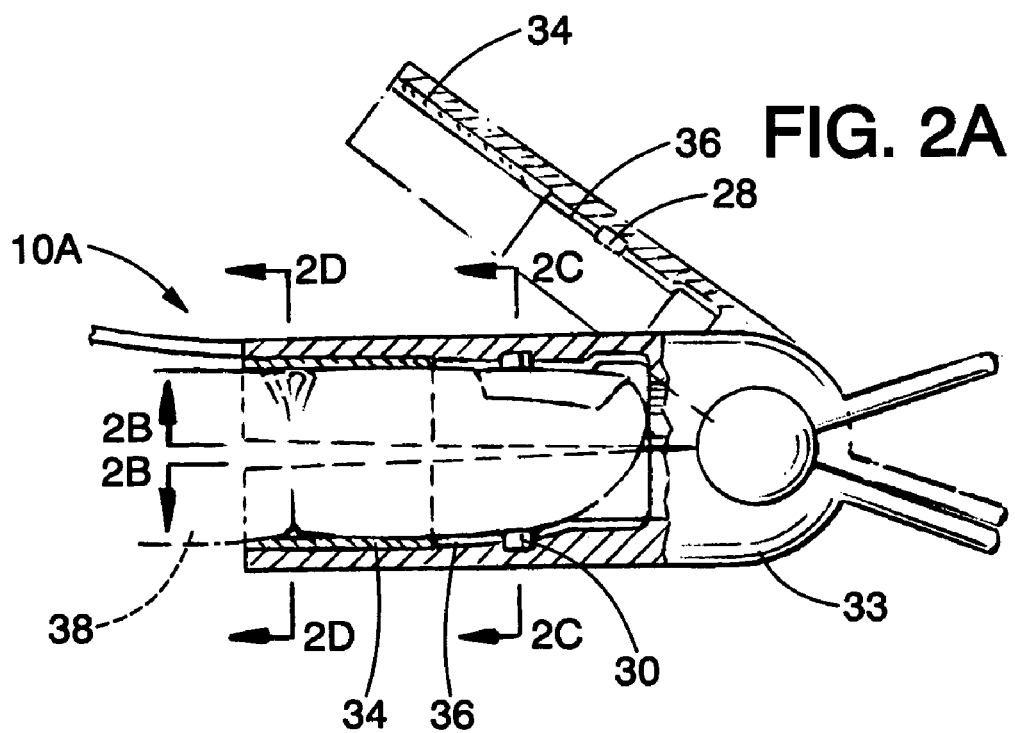
FIG. 2A illustrates an embodiment of an exemplary clip-style sensor adapted for placement on a patient's digit with absorptive portions and reflective portions in accordance with the present invention.

In accordance with exemplary embodiments, a sensor 10A having an emitter 28 and detector 30 is provided that is configured to selectively absorb light in the region of a digit that corresponds to relatively large vascular or dynamic structures. FIGS. 2A through 2E illustrate an exemplary pulse oximetry sensor 10A of this type. The sensor 10A includes regions that differ in the manner in which they reflect and/or absorb light from the emitter 28. More specifically, FIG. 2A illustrates a sensor 10A having on a tissue-contacting surface 32 of the sensor body 33 absorptive portions 34 of relatively light absorbing material in the areas of the sensor 10A configured to be proximate to the large vascular structures when the sensor 10A is applied to a digit. The sensor 10A has reflective portions 36 of relatively reflective material on a tissue-contacting surface 32 of the sensor body 33 proximate to the fingertip region when the sensor 10A is applied to a digit 38.

FIG. 2B shows a top perspective view of a transmission-type clip-style sensor 10A in the open position. Absorptive portions 34 are disposed on a region of the sensor body that generally will contact patient tissue that is proximate to large vascular structures. A reflective portion 36 is disposed on a region of the sensor body that generally will contact patient tissue that does not contain large vascular structures. An emitter 28 and detector 30 are disposed on the sensor body 33 proximate to the reflective portion 36. As depicted, the absorptive portions 34 and reflective portion 36 are superficially disposed on respective surfaces of the sensor body 33 in contact with patient tissue. It should be appreciated the sensor body 33 may be configured such that the absorptive portions 34 and reflective portion 36 extend through the sensor body to the opposing surface (not shown).

FIG. 2C shows a cross-sectional view of the sensor at a fingertip region (e.g. fingertip region 16 as shown in FIG. 1), whereby the sensor 10A is secured to the digit 38 such that the emitter 28 and the detector 30 are on opposing sides of the digit 38. The reflective portion 36 surrounds the digit 38 at a region containing microvasculature 40. FIG. 2D shows a cross-sectional view of the sensor 10A at a region of the digit 38 proximate to large vascular structures. FIG. 2E is a perspective view of the sensor 10A applied to a patient digit 38. As shown in FIGS. 2A-2E, absorptive portions 34 are disposed on opposing faces of the sensor body 33. When applied to the digit 38, absorptive portions 34 substantially surround the digit 38 at a region containing arteries, tendons, ligaments, and bone (e.g. arteries 18, tendons 20, ligaments 22, and bone 24 as shown in FIG. 1), generically referred to here as relatively larger subcutaneous anatomic structures 42. Additionally, the absorptive portions 34 correspond to areas of the skin that may crease in response to flexing of the joint, causing heterogeneity in the surface of the digit in the area covered by the sensor 10A. Consequently, it is more likely that light detected by the detector 30 has passed through tissue in the fingertip region of the patient's finger as opposed to areas containing large vascular structures. Hence, the collected light presumably correlates better with the characteristics of the blood that the pulse oximeter is attempting to measure, since the collected light is not as adversely affected by relatively large vascular structures in the of the digit 38.

Figure 3A:
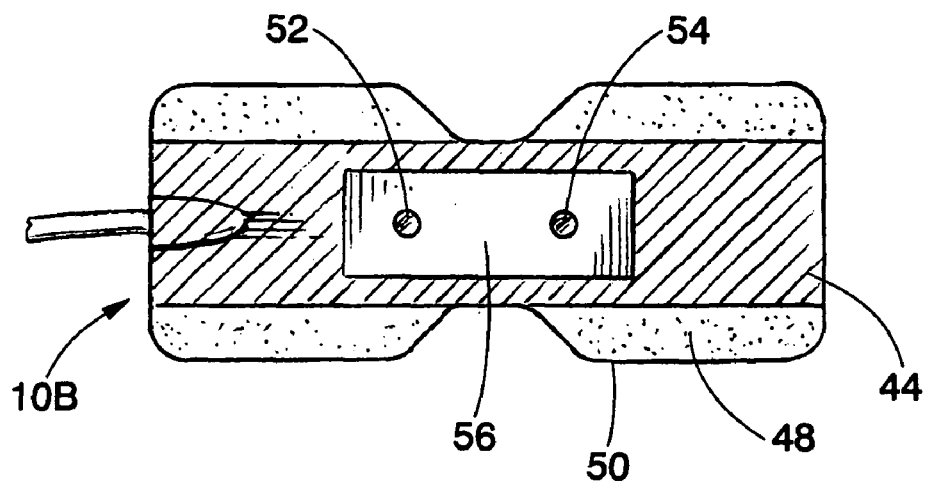
FIG. 3A illustrates an exemplary embodiment of a bandage-style sensor with an absorptive region along the perimeter of the tissue-contacting surface of the sensor in accordance with the present invention.
Figure 3B:
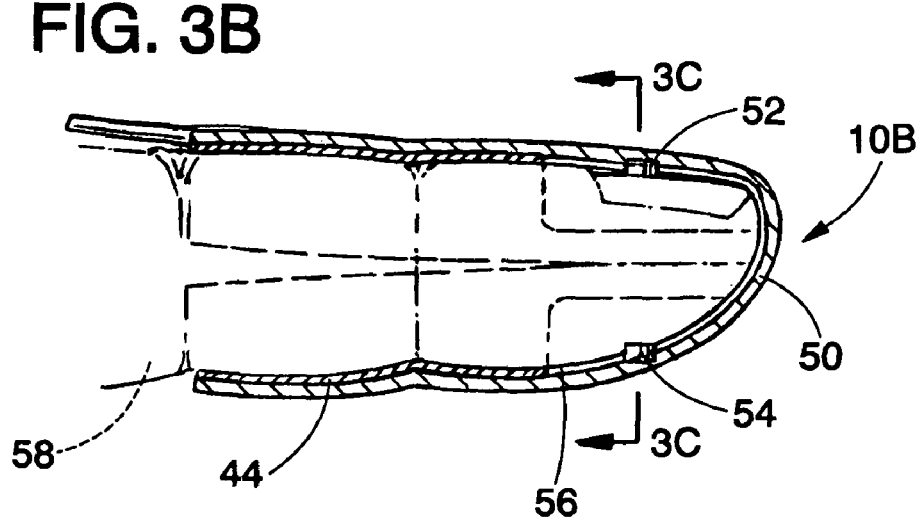
FIG. 3B illustrates a cross-sectional view of the sensor of FIG. 3A applied to a patient's digit in accordance with the present invention.
Figure 3C:
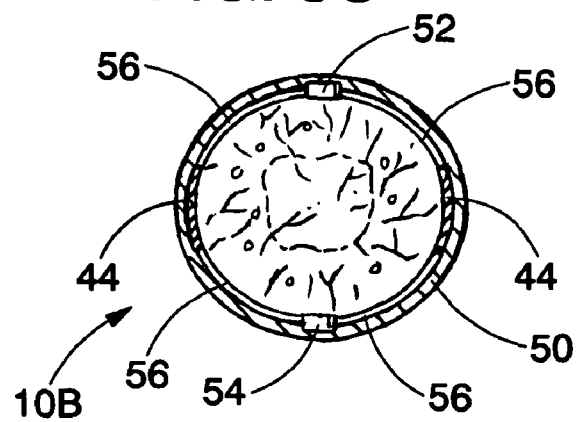
FIG. 3C illustrates a fingertip region cross-section of the sensor of FIG. 3A after placement on a patient's digit.

In certain embodiments, it may be useful to provide an absorptive portion around a perimeter of a sensor to absorb any outside light that might otherwise leak into the sensor. FIG. 3A depicts a transmission-type bandage sensor 10B. As shown in FIG. 3A, the sensor 10B may also include an absorptive portion 44 on a tissue-contacting surface 48 of the sensor body 50 that extends on either side of the emitter 52 and the detector 54 around the perimeter of the sensor body 50. The absorptive portion 44 of the sensor body 50 may serve to absorb incidental outside light that might otherwise leak in and cause variability in measurement. A reflective portion 56 surrounds the emitter 52 and the detector 54. FIG. 3B shows a cross-sectional view of a transmission-type bandage sensor 10B applied to a patient digit 58. When applied to a digit 58, the absorptive portion 44 is proximate to relatively large vascular structures, and further extends along the sides of the digit along the sides of a fingertip region (e.g. fingertip region 16 as shown in FIG. 1), in order to prevent light from leaking into the sensor body. FIG. 3C shows a cross-sectional view of fingertip region of a digit 58, after application the sensor of FIG. 3A. The reflective portion 56 is proximate to the region of the digit containing microvasculature. Absorptive portions 44 are shown as meeting on the sides of the digit 58

Figure 4A:
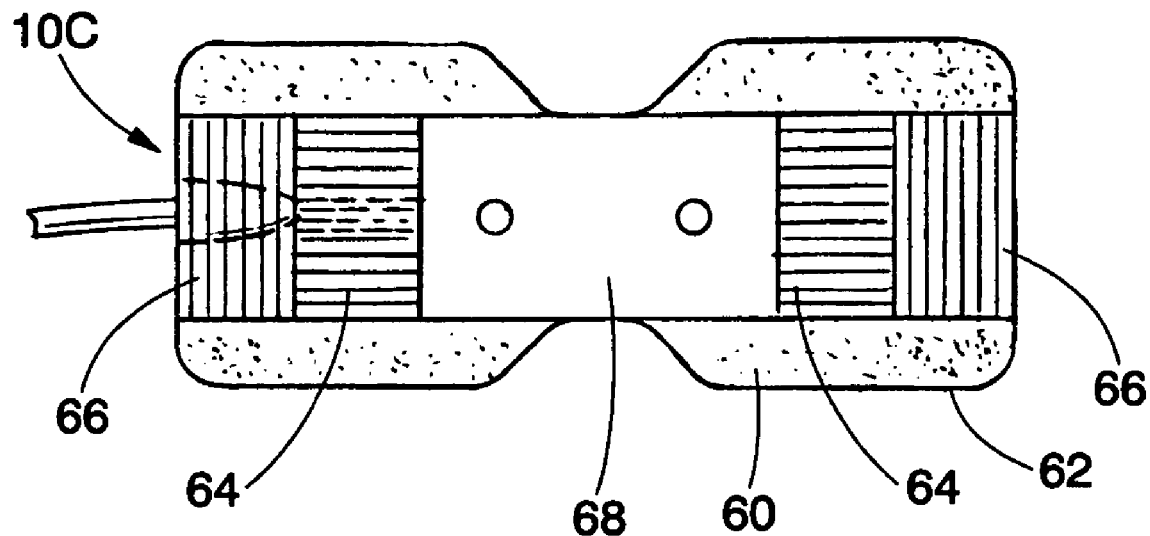
FIG. 4A illustrates an exemplary pulse oximetry sensor with absorptive portions, reflective portions, and a transitional zone in accordance with the present invention.
Figure 4B:
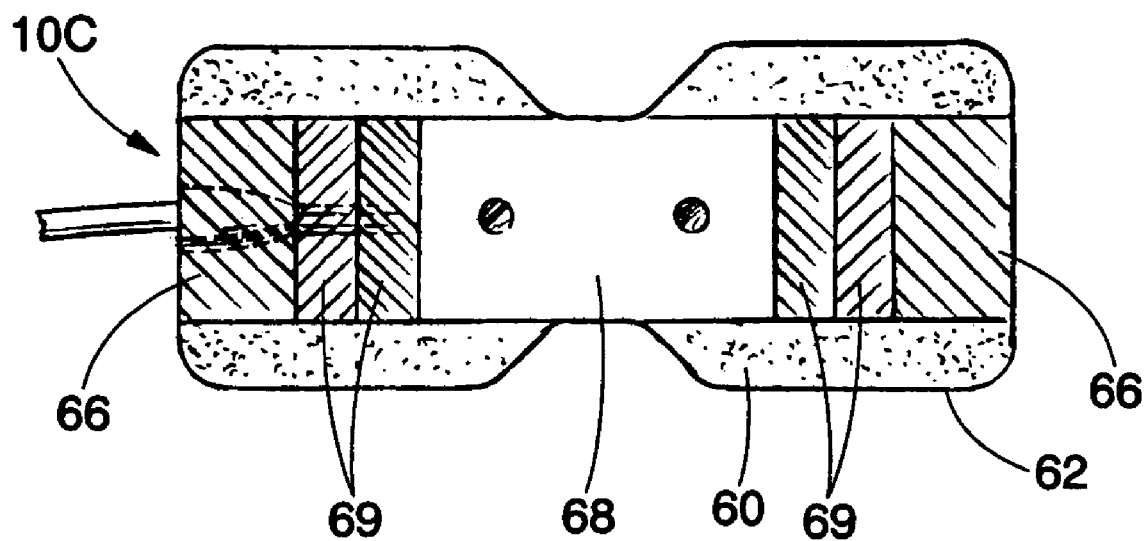

In other embodiments, it may be desirable to provide a transitional region of a sensor that is neither strongly absorptive nor strongly reflective. In FIG. 4A, it can be seen that a sensor 10C with a tissue-contacting surface 60 of the sensor body 62 includes a transitional zone 64 of intermediate reflective and/or absorptive ability situated between the absorptive portion 66, and the reflective portion 68. The transitional zone material that is neither strongly absorptive nor strongly reflective may absorb approximately 30%-49% of the emitted light. For example, a transitional zone may be substantially gray in color. Alternatively, a transitional zone may be transition from an absorptive region by forming a gradient 69 (depicted as two regions which may be sections of the gradient) of black to white as it transitions towards a reflective region, as shown in FIG. 4B. In another embodiment, a transitional zone may have a pattern 70, such as a pattern of black and white stripes, as shown in FIG. 4C.

Figure 5B:
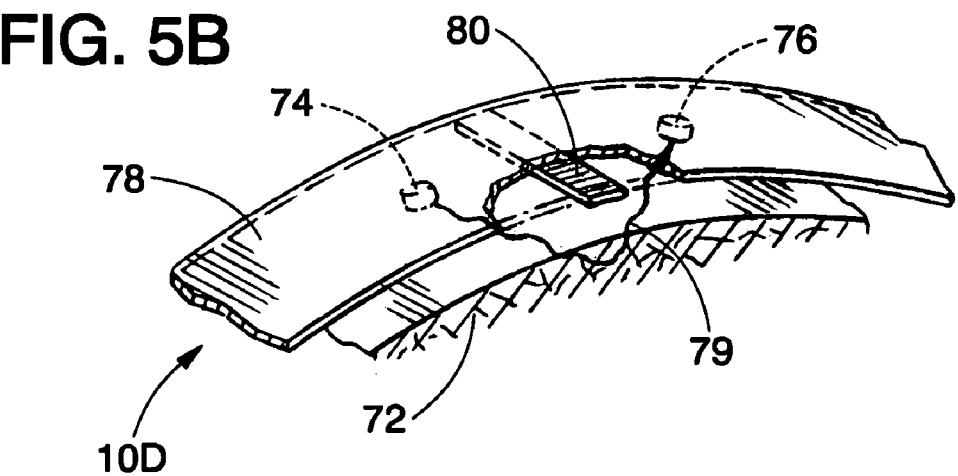
FIG. 5B illustrates the sensor of FIG. 5A with a shunt block.

As discussed above, in certain embodiments, it may be useful to use a reflectance-type pulse oximetry sensor. FIG. 5A illustrates one wrap-style configuration of a reflectance-type sensor 10D on a patient's finger 72. When using reflectance type sensors, it may be useful to block light that may "shunt" directly between the emitter and detector of such a sensor. In one embodiment, the sensor 10D may be adapted to block light that may shunt directly between the emitter 74 and the detector 76, i.e., light that does not travel through the blood perfused tissue of the finger 72. For example, a light shunt may occur when light travels from the emitter 74 to the detector 76 through the sensor body 78. In certain embodiments, as illustrated in FIG. 5B, such a light shunt may be addressed by placing an absorptive region 80 on the sensor body 78 between the emitter 74 and the detector 76. Such an absorptive region 80 would not interfere with the optical path of the signal light, illustrated by wavy arrow 79, as it passes through the patient's finger 72

Figure 6A:
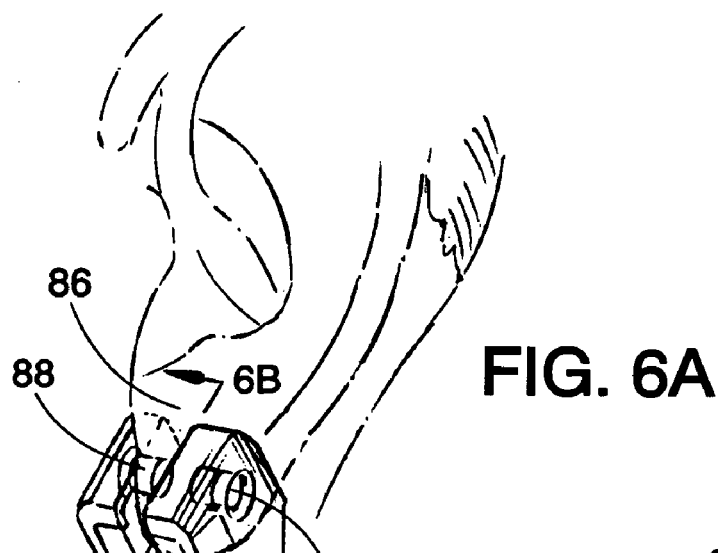
FIG. 6A illustrates a perspective view of an exemplary clip-style sensor applied to an earlobe with absorptive portions surrounding the perimeter of the tissue-contacting surface of the sensor in accordance with the present invention.
Figure 6B:
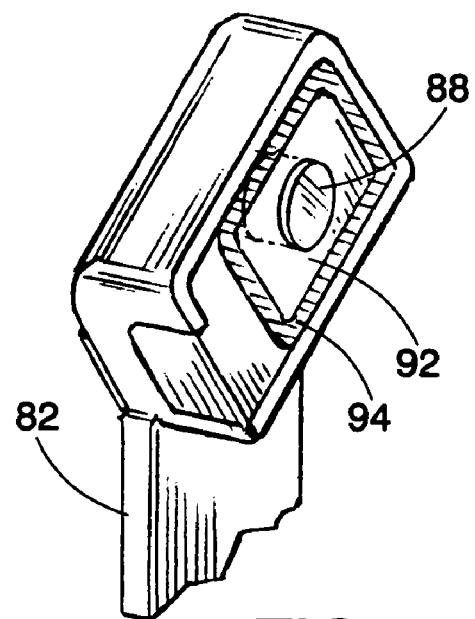
FIG. 6B illustrates a cross-sectional view of the clip-style sensor if FIG. 6A.

As discussed above, it may be useful to adapt a sensor for use on an earlobe, such as the clip-style sensor 10E that is illustrated in FIGS. 6A and 6B. The sensor 10E is illustrated as having portions 82 and 84 that are configured to be applied to a patient's earlobe 86. In this embodiment, the sensor 10E is configured to operate in transmission mode, so the emitter 88 resides in one portion 82 and the detector 90 resides in the other portion 84. The sensor 10E includes a reflective portion 92 and an absorptive portion 94 on the face of each portion 82 and 84 of the clip-style sensor 10E. In the illustrated embodiment, as shown in FIG. 6B, the absorptive portion 94 is configured to ring the perimeter of portions 82 and 84 of the sensor 10E to prevent outside light from leaking into the sensor. In an alternate embodiment (not shown), the sensor 10E may be configured to operate in reflectance mode, in which case the emitter 88 and the detector 90 would reside in the same portion, 82 or 84. In either case, the sensor 10E may be spring loaded so that the sensor 10E is biased in a closed position about an earlobe 86, as illustrated.

It should be appreciated that providing a sensor with the ability to selectively reflect light in certain portions and to selectively absorb light in other portions may be accomplished in a number of ways. For example, a tissue-contacting surface of a sensor body may be formed from, coated with, or impregnated with a light absorbing material (e.g absorptive portions 34, 44, 66, 80, or 94) in certain regions and a light reflective material (e.g. reflective portions 36, 56, 68, or 92) in other regions. It should also be appreciated that, as discussed above, a the sensor body may contain light absorbing material and light reflecting material only on a tissue-contacting surface, or, in alternate embodiments, the sensor body may be constructed entirely from light absorbing material and light reflecting material in appropriate regions. It should be appreciated that the light absorbing material may be adapted to absorb light at a particular wavelength. For example, a light absorbing material may absorb at least about 50% of one or more wavelengths of light from the emitter. A light absorbing material may also absorb at least about 90% or at least 95% of one or more wavelengths of visible light and near-infrared light. Examples of light absorbing materials may include, but are not limited to, black or dark pigment, black or dark woven fabric or cloth, and infrared blockers. A light reflecting material may also reflect at least about 80% of one or more wavelengths of visible light or near-infrared light. Examples of light reflecting materials may include, but are not limited to, white or substantially light pigment, white or light woven fabric or cloth, and metals or metallic foils. Another example of a light reflective material is light reflecting ceramic, such as Accuflect, available from Accuratus.

In certain embodiments, it may be advantageous to provide light absorbing portions and light reflecting portions from a material that varies in its ability to absorb or reflect light in response to certain stimuli. For example, Thermex temperature indicating paper (Sensor Product, Inc., East Hanover, N.J.) changes color in response to variations in temperature. Upon exposure to heat, Thermex paper changes to a blue color. The surface of a patient's tissue corresponding to relatively large subcutaneous structures, such as veins and arteries, may be generally warmer due to an increased volume of blood flow as compared to other tissue sites. Hence, a sensor having Thermex paper on a tissue-contacting surface may be blue, and thus more absorptive, in areas of the sensor corresponding to subcutaneous veins and arteries. A sensor that includes such a temperature-sensitive material incorporated into the sensor body may be useful for improving the signal to noise ratio if a patient experiences low perfusion, such as low perfusion associated with cold temperatures. For example, the temperature-sensitive material may have increased reflectivity in relatively cold temperatures, which may serve to intensify a weaker signal typically associated with low perfusion. Cold temperatures may be temperatures lower than room temperature, or lower than 20-25° C. In a room temperature environment, the temperature-sensitive material may return to a default level of reflectivity. In certain embodiments, the temperature-sensitive material may turn silver upon exposure to relatively cold temperatures and may be white or light grey at room temperature.

Figure 7A:
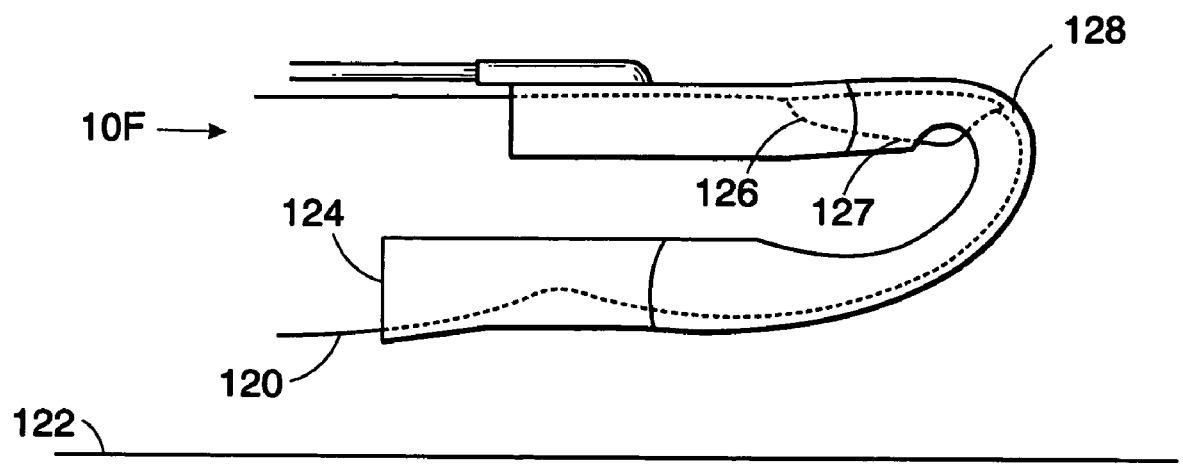
FIG. 7A illustrates a view of an exemplary bandage-style sensor applied to a finger with a pressure-sensitive absorptive portion surrounding the upper nail bed in accordance with the present invention.
Figure 7B:
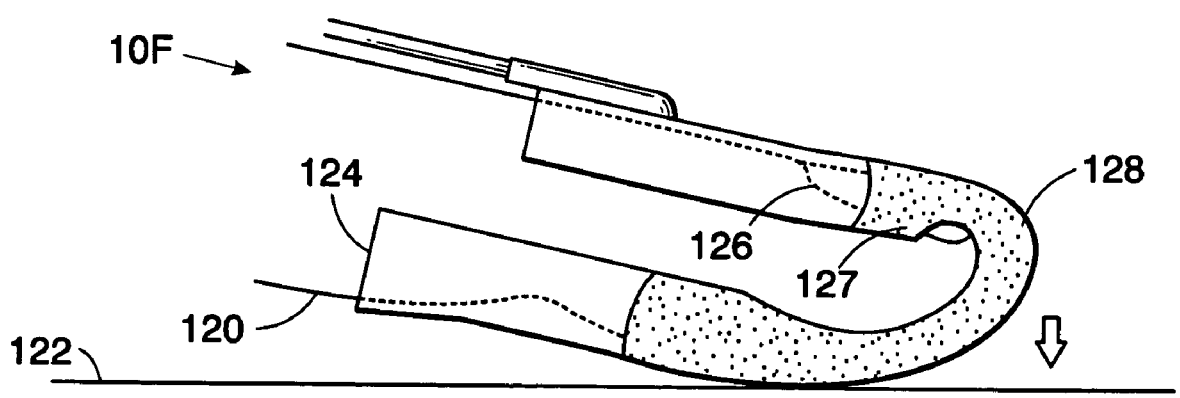
FIG. 7B illustrates the sensor of FIG. 7A after pressure has been applied to the finger.

In another embodiment, light absorbing portions and light reflecting portions of a tissue-contacting surface of a sensor body are made from a pressure-sensitive material, such as PressureX® (Sensor Product, Inc., East Hanover, N.J.), which increases in color intensity in response to increased pressure. As tissue under pressure may become exsanguinated, and thus may shunt light, it may be advantageous to absorb light in areas of the tissue subjected to pressure. In an alternative embodiment, shown in FIGS. 7A and 7B, a sensor 10F may include a pressure-sensitive material 129 that may trigger a color darkening in areas of the sensor body 124 that correspond to areas of the tissue where blood pools after the application of pressure. For example, a pressing down motion of the finger 120 against a rigid object 122 may lead to a pooling of the blood and darkening of an upper portion 127 of the nail bed, while the lower portion 126 of the nail bed experiences no change in color. The color change of the color-changing material 128 may be throughout the sensor body 124, as depicted, or may occur on the tissue-contacting surface of the sensor body 124. The color-changing material 128 is pressure-sensitive, and darkens upon application of pressure. Thus, although the finger 120 may exhibit a change of blood pooling as a function of pressure, the effects of such change on the transmitted light signal may be mitigated by increasing the absorption of light surrounding the pooled blood. Generally, areas of the tissue that are unaffected by an increase in pressure may be surrounded by reflective or intermediately reflective portions of the sensor body 124. The color-changing material may include Pressurex® film, available from Sensor Products Inc. (East Hanover, N.J.), which increases in red color intensity in relation to the amount of force applied.

Figure 8:
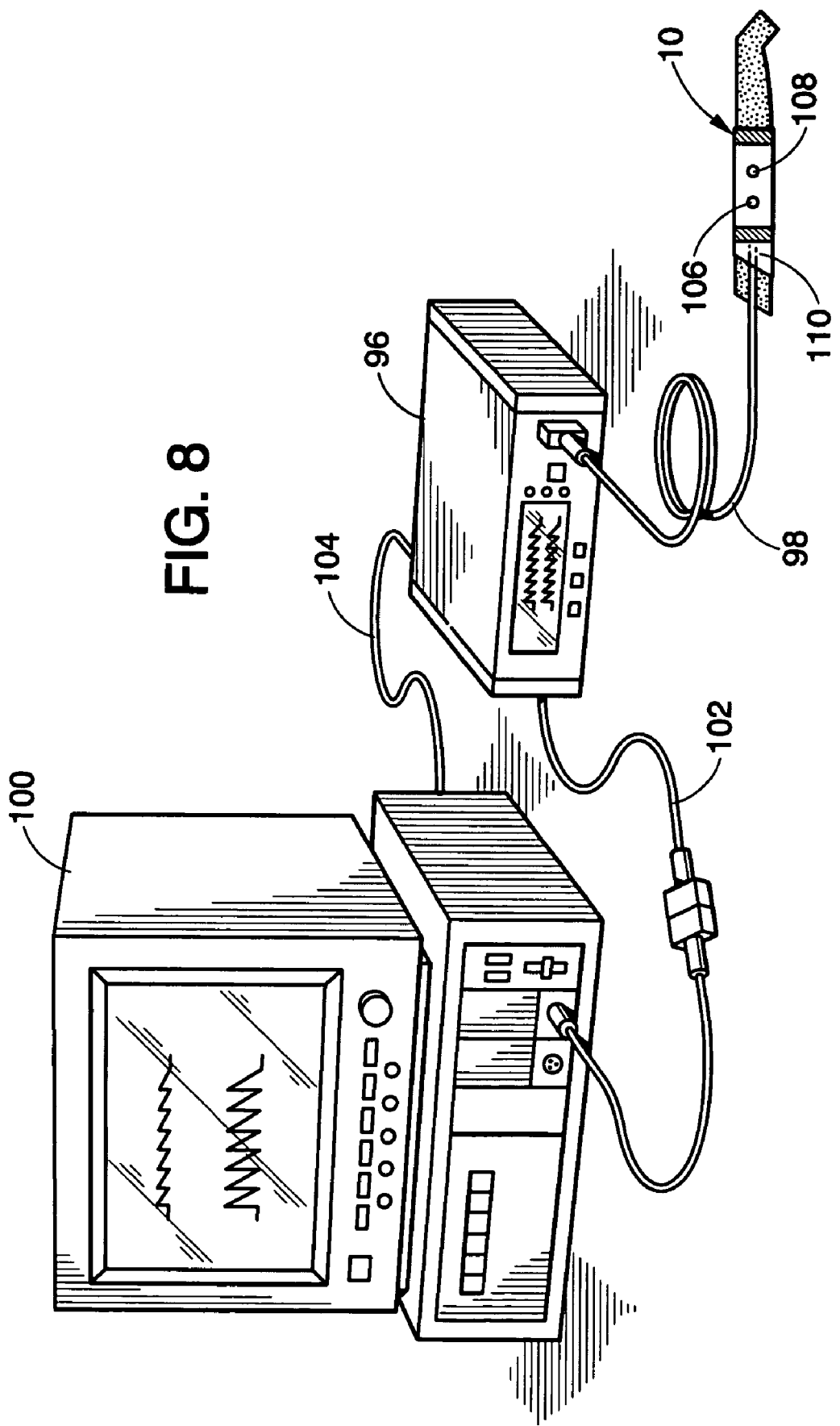
FIG. 8 illustrates a pulse oximetry system coupled to a multi-parameter patient monitor and a sensor according to embodiments of the present invention.

A sensor, illustrated generically as a sensor 10, may be used in conjunction with a pulse oximetry monitor 96, as illustrated in FIG. 8. It should be appreciated that the cable 98 of the sensor 10 may be coupled to the monitor 96 or it may be coupled to a transmission device (not shown) to facilitate wireless transmission between the sensor 10 and the monitor 96. The monitor 96 may be any suitable pulse oximeter, such as those available from Nellcor Puritan Bennett Inc. Furthermore, to upgrade conventional pulse oximetry provided by the monitor 96 to provide additional functions, the monitor 96 may be coupled to a multi-parameter patient monitor 100 via a cable 102 connected to a sensor input port or via a cable 104 connected to a digital communication port.

The sensor 10 includes an emitter 106 and a detector 108 that may be of any suitable type. For example, the emitter 106 may be one or more light emitting diodes adapted to transmit one or more wavelengths of light in the red to infrared range, and the detector 108 may one or more photodetectors selected to receive light in the range or ranges emitted from the emitter 106. Alternatively, an emitter may also be a laser diode or a vertical cavity surface emitting laser (VCSEL). An emitter and detector may also include optical fiber sensing elements. An emitter 106 may include a broadband or "white light" source, in which case the detector could include any of a variety of elements for selecting specific wavelengths, such as reflective or refractive elements or interferometers. These kinds of emitters 106 and/or detectors 108 would typically be coupled to the rigid or rigidified sensor via fiber optics. Alternatively, a sensor 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 106 and the detector 108 may be disposed on a sensor body 110, which may be made of any suitable material, such as plastic, foam, woven material, or paper. Alternatively, the emitter 106 and the detector 108 may be remotely located and optically coupled to the sensor 10 using optical fibers. In the depicted embodiments, the sensor 10 is coupled to a cable 98 that is responsible for transmitting electrical and/or optical signals to and from the emitter 106 and detector 108 of the sensor 10. The cable 78 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 106 and detector 108 that are typically placed on opposing sides of the sensor site. If the sensor site is a fingertip, for example, the sensor 10 is positioned over the patient's fingertip such that the emitter 106 and detector 108 lie on either side of the patient's nail bed. In other words, the sensor 10 is positioned so that the emitter 106 is located on the patient's fingernail and the detector 108 is located 180° opposite the emitter 106 on the patient's finger pad. During operation, the emitter 106 shines one or more wavelengths of light through the patient's fingertip and the light received by the detector 108 is processed to determine various physiological characteristics of the patient. In each of the embodiments discussed herein, it should be understood that the locations of the emitter 106 and the detector 108 may be exchanged. For example, the detector 108 may be located at the top of the finger and the emitter 106 may be located underneath the finger. In either arrangement, the sensor 10 will perform in substantially the same manner.

Reflectance type sensors also operate by emitting light into the tissue and detecting the light that is transmitted and scattered by the tissue. However, reflectance type sensors include an emitter 106 and detector 108 that are typically placed on the same side of the sensor site. For example, a reflectance type sensor may be placed on a patient's fingertip or forehead such that the emitter 106 and detector 108 lie side-by-side. Reflectance type sensors detect light photons that are scattered back to the detector 108. A sensor 10 may also be a "transflectance" sensor, such as a sensor that may subtend a portion of a baby's heel.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood and/or tissue constituents using principles of pulse oximetry. For example, using the same, different, or additional wavelengths, the present techniques may be utilized for the measurement and/or analysis of carboxyhemoglobin, methemoglobin, total hemoglobin, fractional hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
   a sensor body;
   an emitter disposed on the sensor body, wherein the emitter is adapted to transmit light into tissue;
   a detector disposed on the sensor body, wherein the detector is adapted to detect the light;
   a light reflecting material disposed proximate to the emitter and detector on a first portion of a tissue-contacting surface of the sensor body, wherein the detector forms a portion of the tissue-contacting surface; and
   a light absorbing material disposed on a second portion of the tissue-contacting surface of the sensor body, wherein the light absorbing material comprises a temperature-sensitive material capable of changing color in response to a change in temperature, and wherein the second portion is adapted to be positioned proximate to relatively large subcutaneous anatomic structures of the tissue.

2. The sensor, as set forth in claim 1, wherein the sensor comprises at least one of a pulse oximetry sensor or a sensor for measuring a water fraction.

3. The sensor, as set forth in claim 1, wherein the emitter comprises at least one light emitting diode.

4. The sensor, as set forth in claim 1, wherein the detector comprises at least one photodetector.

5. The sensor, as set forth in claim 1, wherein the emitter and detector are adapted to operate in a reflectance mode, and wherein the light absorbing material is disposed in a region between the emitter and the detector.

6. The sensor, as set forth in claim 1, wherein the sensor is adapted to be placed on a patient's finger and the light absorbing material is disposed on the tissue-contacting surface of the sensor body outside a fingertip-contacting region.

7. The sensor, as set forth in claim 6, wherein the light reflecting material is disposed on the fingertip-contacting region of the sensor body.

8. The sensor, as set forth in claim 1, wherein the light reflecting material comprises a metal.

9. The sensor, as set forth in claim 1, wherein the sensor is adapted to be placed on a patient's digit and the light absorbing material is disposed on a region of the sensor body adapted to be positioned along one or both sides of the digit.

10. The sensor, as set forth in claim 1, comprising a material of intermediate absorptive and reflective ability disposed between the light reflecting material and the light absorbing material.

11. The sensor, as set forth in claim 1, wherein the sensor comprises a clip-style sensor body on which the emitter and detector are disposed.

12. The sensor, as set forth in claim 1, wherein the sensor comprises a bandage-style sensor body on which the emitter and detector are disposed.

13. The sensor, as set forth in claim 1, wherein the sensor comprises a wrap-style sensor body on which the emitter and detector are disposed.

14. The sensor, as set forth in claim 1, wherein the sensor body is adapted for use on a patient's forehead.

15. A sensor comprising:
an emitter adapted to deliver light into a tissue, wherein the tissue comprises relatively large subcutaneous anatomic structures and relatively small subcutaneous anatomic structures;
a detector adapted to detect the light; and
a sensor body on which the emitter and detector are disposed, the sensor body having a tissue-contacting surface, wherein the detector forms a portion of the tissue-contacting surface, and wherein the tissue-contacting surface is adapted to absorb light proximate to the relatively large subcutaneous anatomic structures and to reflect light proximate to the relatively small subcutaneous anatomic structures, and wherein the tissue-contacting surface comprises a pressure-sensitive material capable of changing color in response to a change in pressure.

16. The sensor, as set forth in claim 15, wherein the sensor comprises at least one of a pulse oximetry sensor or a sensor for measuring a water fraction.

17. The sensor, as set forth in claim 15, wherein the emitter comprises at least one light emitting diode.

18. The sensor, as set forth in claim 15, wherein the detector comprises at least one photodetector.

19. The sensor, as set forth in claim 15, wherein the relatively large subcutaneous anatomic structures comprise arteries, and wherein the relatively small subcutaneous anatomic structures comprise arterioles or capillaries.

20. The sensor, as set forth in claim 15, wherein the relatively large subcutaneous anatomic structures comprise dynamic structures.

21. The sensor, as set forth in claim 20, wherein the dynamic structures comprise tendons or ligaments.

22. The sensor, as set forth in claim 15, wherein the emitter and detector are adapted to operate in a reflectance mode, and wherein the pressure sensitive material is disposed in a region between the emitter and the detector.

23. The sensor, as set forth in claim 15, wherein a first portion of the tissue-contacting surface comprises a substantially white material that is adapted to reflect light.

24. The sensor, as set forth in claim 23, wherein a second portion of the tissue-contacting surface comprises a substantially dark material that is adapted to absorb light.

25. The sensor, as set forth in claim 15, comprising a clip-style sensor body on which the emitter and detector are disposed.

26. The sensor, as set forth in claim 15, wherein the sensor comprises a bandage-style sensor body on which the emitter and detector are disposed.

27. The sensor, as set forth in claim 15, wherein the sensor comprises a wrap-style sensor body on which the emitter and detector are disposed.

28. A pulse oximetry system comprising:
a pulse oximetry monitor; and
a pulse oximetry sensor adapted to be operatively coupled to the monitor, the
sensor comprising:
a sensor body;
an emitter disposed on the sensor body, wherein the emitter is adapted to transmit light into tissue;
a detector disposed on the sensor body, wherein the detector is adapted to detect the light;
a light reflecting material disposed proximate to the emitter and detector on a first portion of a tissue-contacting surface of the sensor body, wherein the detector forms a portion of the tissue-contacting surface; and
a light absorbing material disposed on a second portion of the tissue-contacting surface of the sensor body, wherein the light absorbing material comprises a temperature-sensitive material capable of changing color in response to a change in temperature, and wherein the second portion is adapted to be positioned proximate to relatively large subcutaneous anatomic structures of the tissue.

29. The pulse oximetry system, as set forth in claim 28, wherein the emitter comprises at least one light emitting diode.

30. The pulse oximetry system, as set forth in claim 28, wherein the detector comprises at least one photodetector.

31. The pulse oximetry system, as set forth in claim 28, wherein the emitter and detector are adapted to operate in a reflectance mode, and wherein the light absorbing material is disposed in a region between the emitter and the detector.

32. The pulse oximetry system, as set forth in claim 28, wherein the sensor is adapted to be placed on a patient's finger and the light absorbing material is disposed on the tissue-contacting surface of the sensor body outside a fingertip-contacting region.

33. The pulse oximetry system, as set forth in claim 32, wherein the light reflecting material is disposed on the fingertip-contacting region of the sensor body.

34. The pulse oximetry system, as set forth in claim 28, wherein the light reflecting material comprises a metal.

35. The pulse oximetry system, as set forth in claim 28, wherein the sensor is adapted to be placed on a patient's digit and the light absorbing material is disposed on a region of the sensor body adapted to be positioned along one or both sides of the digit.

36. The pulse oximetry system, as set forth in claim 28, comprising a material of intermediate absorptive and reflective ability disposed between the light reflecting material and the light absorbing material.

37. A method comprising:
delivering light through a patient's tissue;
detecting the light through a patient's tissue with a detector, the detector configured to form a portion of a tissue-contacting surface of a sensor;
absorbing the light with an absorptive material disposed on the tissue-contacting surface proximate to relatively large vascular structures; and
reflecting the light with a reflective material disposed on the tissue-contacting surface proximate to relatively small vascular structures, and wherein the reflective material comprises a material capable of changing reflectivity in response to a change in pressure.

38. The method, as set forth in claim 37, wherein absorbing the light proximate to relatively large vascular structures comprises absorbing the light proximate to veins or arteries and wherein reflecting the light proximate to relatively small vascular structures comprises reflecting the light proximate to arterioles or capillaries.

39. The method, as set forth in claim 37, wherein absorbing the light proximate to relatively large vascular structures comprises absorbing the light proximate to tendons or ligaments.

40. The method, as set forth in claim 37, wherein reflecting the light with reflective material comprises reflecting the light with a substantially white material.

41. The method, as set forth in claim 37, wherein the patient's tissue comprises a finger, and wherein reflecting the light proximate to relatively small vascular structures comprises reflecting the light proximate to the fingertip region of the finger.

42. The method, as set forth in claim 37, wherein absorbing the light with an absorbing material comprises absorbing the light with a substantially dark pigmented material.

43. The method, as set forth in claim 37, comprising absorbing the light from outside sources.

44. A method of manufacturing a sensor, the method comprising:
providing a sensor body;
providing an emitter adapted to transmit light into tissue;
providing a detector adapted to detect the light;
providing a light reflecting material disposed proximate to the emitter and detector on a first portion of a tissue-contacting surface of the sensor body, wherein the detector forms a portion of the tissue-contacting surface; and
providing a light absorbing material disposed on a second portion of the tissue-contacting surface of the sensor body, wherein the second portion is adapted to be positioned proximate to relatively large subcutaneous anatomic structures of the tissue, and wherein the light absorbing material comprises a temperature-sensitive material capable of changing absorptivity in response to a change in temperature.

45. The method, as set forth in claim 44, comprising:
disposing the emitter and the detector on a clip-style sensor body.

46. A method comprising:
delivering light through a patient's tissue; and
reflecting the light with a temperature-sensitive material adapted to have increased reflectivity when exposed to relatively low temperatures.

47. The method, as set forth in claim 46, wherein the temperature-sensitive material has increased reflectivity at temperatures lower than 20° C.

48. A method comprising:
delivering light through a patient's tissue; and
absorbing the light with a material adapted to have increased absorption after receiving a feedback related to pressure.

49. The method, as set forth in claim 48, wherein the material is capable of increasing a color intensity after receiving the feedback related to pressure.

50. A sensor comprising:
a sensor body;
an emitter disposed on the sensor body, wherein the emitter is adapted to transmit light into tissue;
a detector disposed on the sensor body, wherein the detector is adapted to detect the light;
a temperature-sensitive material disposed on the sensor body, wherein the temperature-sensitive material is capable of increasing in absorptivity or reflectivity upon experiencing a change in temperature.

51. The sensor, as set forth in claim 50, wherein the temperature-sensitive material is capable of changing color upon experiencing the change in temperature.

52. The sensor, as set forth in claim 50, wherein the temperature-sensitive material is capable of increasing in reflectivity when exposed to relatively low temperature.

53. The sensor, as set forth in claim 50, wherein the pressure-sensitive material is capable of changing color upon experiencing the change in pressure.

54. The sensor, as set forth in claim 50, wherein the pressure-sensitive material is capable of increasing in absorptivity upon experiencing the change in pressure.

55. A sensor comprising:
a sensor body;
an emitter disposed on the sensor body, wherein the emitter is adapted to transmit light into tissue;
a detector disposed on the sensor body, wherein the detector is adapted to detect the light;
a pressure-sensitive material disposed on the sensor body, wherein the pressure-sensitive material is capable of increasing in absorptivity or reflectivity upon experiencing a change in pressure.

56. A sensor comprising:
a sensor body;
an emitter disposed on the sensor body, wherein the emitter is adapted to transmit light into tissue;
a detector disposed on the sensor body, wherein the detector is adapted to detect the light;
a light reflecting material disposed proximate to the emitter and detector on a first portion of a tissue-contacting surface of the sensor body, wherein the detector forms a portion of the tissue-contacting surface; and
a light absorbing material disposed on a second portion of the tissue-contacting surface of the sensor body, wherein the light absorbing material comprises a pressure-sensitive material capable of changing color in response to a change in pressure.

57. A pulse oximetry system comprising:
a pulse oximetry monitor; and
a pulse oximetry sensor adapted to be operatively coupled to the monitor, the
sensor comprising:
a sensor body;
an emitter disposed on the sensor body, wherein the emitter is adapted to transmit light into tissue;

a detector disposed on the sensor body, wherein the detector is adapted to detect the light;

a light reflecting material disposed proximate to the emitter and detector on a first portion of a tissue-contacting surface of the sensor body, wherein the detector forms a portion of the tissue-contacting surface; and a light absorbing material disposed on a second portion of the tissue-contacting surface of the sensor body, wherein the light absorbing material comprises a pressure-sensitive material capable of changing color in response to a change in pressure.

58. A sensor comprising:

an emitter adapted to deliver light into a tissue;

a detector adapted to detect the light; and a sensor body on which the emitter and detector are disposed, the sensor body having a tissue-contacting surface, wherein the detector forms a portion of the tissue-contacting surface, and wherein the tissue-contacting surface is adapted to absorb light and to reflect light, and wherein the tissue-contacting surface comprises a temperature-sensitive material capable of changing color in response to a change in temperature.

59. A method of manufacturing a sensor, the method comprising:

providing a sensor body;

providing an emitter adapted to transmit light into tissue;

providing a detector adapted to detect the light;

providing a light reflecting material disposed proximate to the emitter and detector on a first portion of a tissue-contacting surface of the sensor body, wherein the detector forms a portion of the tissue-contacting surface; and providing a light absorbing material disposed on a second portion of the tissue-contacting surface of the sensor body, wherein the second portion is adapted to be positioned proximate to relatively large subcutaneous anatomic structures of the tissue, and wherein the light absorbing material comprises a pressure-sensitive material capable of changing absorptivity in response to a change in pressure.

60. A method comprising:

delivering light through a patient's tissue; and absorbing the light with a material adapted to change absorptivity after receiving a feedback related to a change in temperature.

* * * * *